United States Patent [19]

Shirasaki et al.

[11] Patent Number: 5,182,276
[45] Date of Patent: Jan. 26, 1993

[54] NOOTROPIC AGENT

[75] Inventors: Yasufumi Shirasaki; Shinichiro Ashida, both of Tokyo, Japan

[73] Assignees: Santen Pharmaceutical Co., Ltd., Osaka; Daiichi Pharmaceutical Co., Ltd., Tokyo, both of Japan

[21] Appl. No.: 623,657

[22] PCT Filed: Jun. 14, 1990

[86] PCT No.: PCT/JP90/00773
§ 371 Date: Dec. 27, 1990
§ 102(e) Date: Dec. 27, 1990

[87] PCT Pub. No.: WO90/15607
PCT Pub. Date: Dec. 27, 1990

[30] Foreign Application Priority Data

Jun. 16, 1989 [JP] Japan .................. 1-153646

[51] Int. Cl.$^5$ .................. A61K 31/54; C07D 279/16
[52] U.S. Cl. .................. 514/224.2; 544/52
[58] Field of Search .................. 544/52; 514/224.2

[56] References Cited

U.S. PATENT DOCUMENTS 3,166,554  1/1965  Krapcho ................ 260/243
4,640,916  2/1987  Meguro et al. ........... 514/645
4,654,372  3/1987  Marcoux ................ 514/646,

FOREIGN PATENT DOCUMENTS 2111728 10/1971 France .
WO90/15607 12/1990 PCT Int'l Appl. .
WO87/838 12/1987 World Int. Prop. O. .

OTHER PUBLICATIONS

Hata, *Medical Pharmacy*, 1991, 25:33(85)–39(92).
Wauquier et al, The Japanese Journal of Pharmacology, vol. 38, No. 1, (1985) 1–7, "'Calcium Entry Blockers'" as Cerebral Protecting Agents: Comparative Activity in Tests of Hypoxia and Hyperexcitability.
Reynolds, Martindale—The Extra Pharmacopoeia, 29th Edition, p. 1492 "Vasodilators".
Yoshztomi Seiyaku K.K., Patent Abstenactz of Japan, vol. 5, No. 111, (1981), "Benzothiazine Derivative".

*Primary Examiner*—John M. Ford
*Attorney, Agent, or Firm*—Burns, Doane, Swecker & Mathis

[57] ABSTRACT

The present invention relates to a nootropic agent which comprises a derivative of 2-phenyl-3-oxo-2H-1,4-benzothiazine. This nootropic agent is effective for treating diseases accompanied by a lowering of cerebral functions, for instance, cerebral infarction disorders due to ischemia such as transitory cerebral ischemia, brain edema, cerebral disorders due to the after-effect such as cerebral hemorrhage, cerebral disorders due to traumatic injury such as bruise, central nervous degeneration and degenerative diseases such as dementia, mental disorders, neurosis and Alzheimer's diseases.

4 Claims, No Drawings

NOOTROPIC AGENT

TECHNICAL FIELD

The present invention relates to a nootropic agent which comprises a derivative of 2-phenyl-3-oxo-2H-1,4-benzothiazine, for instance, a nootropic agent which is effective in treating or presenting diseases accompanied by a lowering of cerebral functions such as cerebral infarction and transitory cerebral ischemic attack.

BACKGROUND ART

In Japan, the average span of human life has been increased and correspondingly patients suffering from diseases accompanied by a lowering of cerebral functions such as dementia, mental disorder, neurosis or the like associated with after-effects of cerebral infarction, cerebral arterial sclerosis or the like have been rapidly increased. This has become a serious social problem.

There have been compelling demands for the development of a medicine which shows excellent effect of treating or improving these diseases accompanied by the lowering of cerebral functions, but there has not yet been proposed any medicine exhibiting a satisfied effect for these diseases.

On the other hand, Japanese Patent Unexamined Publication (hereinafter referred to as "J.P. KOKAI") No. Sho 62-123181 discloses that a derivative of 2-phenyl-3-oxo-2H-1,4-benzothiazine represented by the following general formula (I) exhibits a platelet aggregation inhibiting effect and calcium antagonism and is useful as an agent for treating circulatory diseases, but does not disclose or suggest, at all, that the derivative be effective as a nootropic agent.

DISCLOSURE OF THE INVENTION

The inventors of this invention have conducted various studies to solve the foregoing problems, have found out that the compound represented by the general formula (I) disclosed in J.P. KOKAI No. Sho 62-123181 has an excellent effect as nootropic agent and thus have completed the present invention.

Accordingly, the present invention provides a nootropic agent which comprises, as an effective component, a compound represented by the following general formula (I) or salts thereof

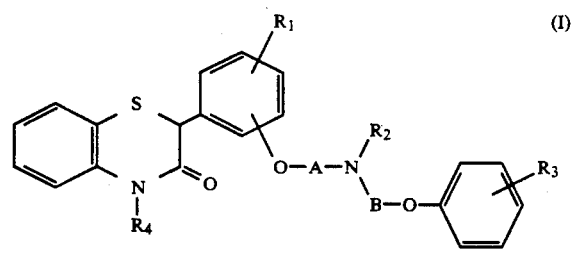

wherein $R_1$ represents one or more of groups selected from the group consisting of a hydrogen atom, a lower alkyl group, a halogen atom, a nitro group, a hydroxyl group, a lower alkoxy group, a lower alkanoyloxy group, an amino group, a lower alkylamino group and a lower alkoxycarbonyloxy group; $R_2$ represents a hydrogen atom, a lower alkyl group or a cycloalkyl group having 3 to 6 carbon atoms; $R_3$ represents one or more groups selected from the group consisting of a hydrogen atom, a lower alkyl group, a halogen atom, a nitro group, a hydroxyl groups a lower alkoxy group, a lower alkylenedioxy group, a lower alkanoyl group, a lower alkanoyloxy group, an amino group, a lower alkylamino group, a lower alkanoylamino group and a lower alkoxycarbonyloxy group, or a group:

$R_4$ represents a hydrogen atom or a lower alkyl group; A and B may be the same or different and each represents a lower alkylene group having 1 to 6 carbon atoms; and n is 3 or 4].

BEST MODE FOR CARRYING OUT THE INVENTION

In Formula (I), the term "a lower alkyl group" means an alkyl group having 1 to 6 carbon atoms such as a methyl, ethyl, propyl and hexyl groups; the term "a halogen atom" means a fluorine, chlorine, bromine atom or the like; the term "a lower alkoxy group" means an alkoxy group having 1 to 6 carbon atoms such as methoxy, ethoxy, propoxy and hexyloxy groups; and the term "a lower alkanoyloxy group" means alkanoyloxy group having 1 to 6 carbon atoms such as acetyloxy, propionyloxy and hexanoyloxy groups. Examples of the cycloalkyl groups having 3 to 6 carbon atoms are cyclopropyl group, cyclohexyl groups and the like. The term "a lower alkylenedioxy group" means a group formed by bonding each of two oxygen atoms to the terminal carbon atoms of an alkylene group having 1 to 6 carbon atoms such as methylenedioxy and ethylenedioxy groups; and the term "a lower alkanoyl group" means an alkanoyl group having 1 to 6 carbon atoms such as an acetyl, propionyl and hexanoyl groups.

Examples of the salts of the compounds of Formula (I) include pharmaceutically acceptable salts thereof with inorganic acid or organic acid such as hydrochloric acid, sulfuric acid, phosphoric acid, lactic acid, maleic acid, fumaric acid, oxalic acid, methanesulfonic acid and p-toluenesulfonic acid.

The compounds of Formula (I) have stereoisomers and they are all included in the scope of this invention.

The compounds of Formula (I) which exhibit preferred nootropic effect are those of Formula (I) wherein $R_1$ is a lower alkoxy group, $R_2$ represents a lower alkyl group, $R_3$ is a lower alkylenedioxy group and $R_4$ is a lower alkyl group and salts thereof. Among these, the compounds of Formula (I) wherein $R_1$ is a methoxy group, $R_2$ is a methyl group, $R_3$ is a methylenedioxy group and $R_4$ is a methyl group and their optical isomers as well as their salts exhibit particularly preferred effects.

Examples of the diseases accompanied by a lowering of cerebral functions which are improved or treated according to the present invention are, in addition to the foregoing cerebral infarction and the disorders due to ischemia such as transitory cerebral ischemic attack, brain edema, cerebral disorders due to the after-effect such as cerebral hemorrhage, cerebral disorders due to traumatic injury such as bruise, central nervous degeneration and degenerative diseases such as dementia, mental disorders, neurosis and Alzheimer's diseases.

The compounds of Formula (I) and salts thereof can be formed into various pharmaceutical preparations such as tablets, capsules, granules, powder, supposition and injections together with diluents and/or carriers such as vehicles, disintegrators, stabilizers, binders or the like according to the known pharmaceutical techniques.

The compounds of Formula (I) and salts thereof can generally be administered through oral routes or parenteral routes such as intravenous injection. The dose thereof varies depending on the dosage forms of the preparations and conditions of patients to be treated. When they are administered through oral route, it is in general ranges from 1 to 5,000 mg/day and preferably 10 to 1,000 mg/day for adults, which are administered as a single dose or as several portions per day.

The acute toxicity thereof was investigated by orally administering the compounds of Formula (I) to rats and they were confirmed to be highly safe.

EFFECTS OF THE INVENTION

The compounds of Formula (I) and salts thereof substantially extended the life time of test animals induced by cerebral tissue injury under a hypoxic condition (low oxygen supply) and exhibited strong brain-protecting effect (hypoxia inhibiting effect). Moreover, the compounds of Formula (I) and salts thereof substantially improved ischemic cerebral disorder pathema, energy metabolic disorder of animal brains and impairment of learning and memory functions. In addition, the compounds of Formula (I) and salts thereof substantially enhanced the activity of choline acetyl transferase (ChAT) in animals induced by cerebral disorder. Thus, the compounds of Formula (I) and salts thereof are effective as nootropic agents, i.e., agents for treating or preventing diseases accompanied by the lowering of cerebral functions as well as therapeutic or preventing agents for ischemic cerebral diseases.

The present invention will hereinafter be explained in more detail with reference to the following Examples, but the present invention is not restricted to these Examples.

EXAMPLE 1

Test of Hypoxia-Inhibiting Effect

In this test, groups (9 to 10 mice each) of ICR mice were employed. The compound to be tested was suspended in a 0.5% aqueous methyl cellulose solution and was orally administered. 60 Minutes after the administration, each mouse was placed in a transparent container (volume 500m $\mu$) having an exhaust hole and N, gas was supplied to the container at a rate of 5$\mu$/min. The time (survival time in sec.) ,elapsed from the initiation of the nitrogen gas supply until the cessation of breathing of each mouse was determined. As the compounds to be tested, there was used (+)-3,4-dihydro-2-(5-methoxy-2- (3-(N-methyl-N-[2-[(3,4]propoxy]-phenyl]-4-methyl-3-oxo-2H-1,4-benzothiazine fumarate (hereinafter referred to as "Compound A") which is a representative compound of the present invention. The results obtained are listed in the following Table 1.

TABLE 1

| Group | Dose (Oral Route) | Survival Time (sec) |
|---|---|---|
| Control | solvent | 25.8 ± 0.61 |
| Compound A | 100 mg/kg | 35.7 ± 1.28** |

The numerical value in Table 1 means average ± standard error.
**: P < 0.01 vs. Control (one-way layout variance analysis and Fisher's LSD).
Solvent: 0.5% aqueous methyl cellulose solution.

As seen from the foregoing Table 1, it was confirmed that Compound A (100 mg/kg) shows a significant effect of extending survival time under low oxygen supply condition and thus has a brain-protective effect.

EXAMPLE 2

Test or Cerebral Energy Metabolism

24-Week-old male SHR's were fixed on the back thereof under with 1.5% halothane anesthetic (70% N,O, 30% O$_2$) and the neck thereof was subjected to a median incision. The cerebral ischemia was caused by immediately ligating bilateral common carotid artery with a silk fiber just before the recovery from the anesthetic state. 3.5 Hours after the ligation, the animals were sacrificed by irradiating them with microwaves (5 KW, 1.5 second). The brain tissues were collected and divided into cerebral cortex, hippocampus and striatum. The brain tissues were homogenized in a 0.6N aqueous perchloric acid solution and centrifuged at 3,000 rpm for 20 minutes. The resulting supernatant was used as the sample for detecting the energy metabolic substances. In the measurement, ATP-Uv test (available from Sigma Co., Ltd.) was used as ATP and lactate-UV test (available from Boeringer Mannheim Yamanouchi Co., Ltd.) was used as lactate. The detection of ADP and AMP was performed according to the method of Bergmeyer (Klin. Chem. Klin. Biochem., 1975, 13, p. 507). The energy charge (hereinafter referred to as "E.C.") which served as an indication of the degree of energy sufficiency due to high energy phosphoric acid of adenine nucleotide was calculated from the following relation according to the method of Atkinson (J. Biol. Chem., 1967, 242, p. 3329):

$$E.C.=(ATP+\tfrac{1}{2}ADP)/(ATP+ADP+AMP)$$

In the test, the compound to be tested was suspended in a 0.5% aqueous solution of methyl cellulose and was administered, through an oral route, to the animals to be tested 30 minutes before the ligation of the both common carotid arteries. The results obtained are listed in the following Tables 2 and 3.

TABLE 2

| Group | Dose (Oral route) | ATP (n mole/mg Protein) | Lactate (n mole/mg Protein) | Lactate/Pyruvate |
|---|---|---|---|---|
| Pseudo-operated Group | — | 15.9 ± 1.14** | 31.4 ± 4.52** | 13.0 ± 1.94** |
| Pathema Control | solvent | 10.0 ± 1.03 | 128.6 ± 15.84 | 40.3 ± 6.78 |
| Compound A | 25 mg/kg | 16.9 ± 0.87** | 62.3 ± 10.20** | 19.1 ± 2.71** |

The numerical value in Table 2 means average ± standard error.
*: P < 0.05
**: P < 0.01 vs. Pathema Control Group (one-way layout variance analysis and Fisher's LSD).
Solvent: 0.5% aqueous methyl cellulose solution.

The numerical value in Table 2 means average ± standard error.
*:P<0.05

**: P<0.01 vs. Pathema Control Group (one-way layout variance analysis and Fisher's LSD).
Solvent: 0.5% aqueous methyl cellulose solution.

TABLE 3

| Group | Dose (Oral route) | Cerebral Cortex E.C. | Hippocampus E.C. | Striatum E.C. |
| --- | --- | --- | --- | --- |
| Pseudo-operated | — | 0.759 ± 0.0146** | 0.766 ± 0.009** | 0.770 ± 0.014** |
| Pathema Control | solvent | 0.631 ± 0.0243 | 0.628 ± 0.026 | 0.679 ± 0.032 |
| Compound A | 10 mg/kg | 0.705 ± 0.0237** | 0.706 ± 0.025** | 0.703 ± 0.025** |
| Compound A | 30 mg/kg | 0.764 ± 0.0078** | 0.762 ± 0.022** | 0.768 ± 0.0063** |

The numerical value in Table 3 means average ± standard error.
**: P < 0.01 vs. Pathema Control Group (one-way layout variance analysis and Fisher's LSD).
Solvent: 0.5% aqueous methyl cellulose solution.

As seen from the foregoing Tables, a marked decrease in ATP which served as an indicator of the energy metabolic condition in the brain and a marked increase in lactate which likewise served as an indicator of the anaerobic glycolysis were observed when the both common carotid arteries was ligated for 3.5 hours. On the contrary, Compound A (25 mg/kg) significantly inhibited such changes in the ATP and the lactate due to the ischemia and further substantially improved the ratio, lactate/pyruvate (see Table 2).

In addition, the E.C.'s in the cerebral cortex, hippocampus and striatum were significantly decreased due to the cerebral ischemia and in turn the energy metabolic condition in the brain was substantially impaired by the reduction in the E.C. Contrary to this, Compound A (30 mg/kg) completely inhibited the reduction in the E.C. due to the ischemia and it was also confirmed that Compound A (10 mg/kg) also significantly improved the reduction in the E.C. in the cerebrum cortex and the hippocampus (see Table 3).

EXAMPLE 3

Test of Impairement of Memory and Learning Functions

25-Week-old male SHR's were fixed on the back thereof under anesthetization with 1.5% halothane anesthetic (70% N,O, 30% O$_2$) and the neck thereof was subjected to a median incision. The cerebral ischemia was caused by immediately ligating the both common carotid arteries with a silk fiber after a vinyl tube was attached to the artery and just before the recovery from the anesthetic state. 3.5 Hours after the ligation, the silk fiber was cut to again initiate the blood circulation. In the test, the compound to be tested was suspended in a 0.5% aqueous solution of methyl cellulose and was initially administered, through oral route, to the animals to be tested 30 minutes before the ligation of the common artery and thereafter it was continuously administered every day over 16 days through oral route provided that the compound was not administered during the behavioral pharmacologic tests of the animals and was administered after completion of the tests.

1) Influence on Water Maze-Learning Test

This water maze-learning test was initiated on 7th day after the cerebral ischemia condition was formed. A cylindrical water tank having a diameter of 1.2 m was filled with black water and the temperature thereof was maintained at 20±1° C. A platform which was submerged in the water to a depth of 2 cm and could not be externally seen through the water (hereinafter referred to as "platform") was placed at the central point existing between the center of the water tank and the wall thereof.

The water maze-learning test was performed once a day (one session) which was continuously performed over three days (three sessions). In the first session (1st day), the animal was allowed to freely swim in the water tank which was free of platforms, then a platform was positioned in the tank and the animal was allowed to learn the presence of the platform of refuge by placing the animal thereon for 30 seconds. The animal was released through four predetermined points on the wall of the water tank over four times and the total time (swimming time (sec)) required until the animal got on the platform over four trials was determined. After the four trials, the animal was again allowed to stand on the platform for 30 minutes and thus the first session was completed. In this respect, the maximum total time required over four trials was determined to be 180 seconds. If the test animal failed to complete the trials within 180 seconds, the trial was interrupted at this time, the animal was then allowed to stand on the platform for 30 minutes and the first session was thus finished. The 2nd and 3rd sessions were performed under the same conditions used in the first session except that the test animal was not allowed to freely swim in the water tank prior to the initiation of the test. The spatial positions of the water tank and the platform in the laboratory were not changed at all during the water maze-learning test term. The results obtained are summarized in the following Table 4.

TABLE 4

| Group | Dose (Oral) | Swimming Time (sec.) | | |
| --- | --- | --- | --- | --- |
| | | 1st Session | 2nd Session | 3rd Session |
| Pseudo-operated | — | 92.0 ± 17.69** | 29.4 ± 2.34** | 17.1 ± 2.95** |
| Pathema Control | Solvent | 167.5 ± 9.59 | 130.0 ± 17.13 | 114.9 ± 16.93 |
| Compound A | 10 mg/kg | 105.8 ± 16.50** | 61.4 ± 15.06** | 40.9 ± 11.82** |
| Compound A | 30 mg/kg | 97.2 ± 18.85** | 59.6 ± 9.60** | 34.5 ± 3.60** |

The numerical value in Table 4 means average ± standard error.
*: P < 0.05
**: P < 0.01 vs. Pathema Control Group (one-way layout variance analysis and Fisher's LSD).
Solvent: 0.5% aqueous methyl cellulose solution.

As seen from Table 4, the time required for the SHR group (pathema control group) whose the both common carotid arteries had been ligated for 3.5 hours to reach the base is longer than that for the pseudo-operated group. This indicates that the learning and memory functions of the animal was damaged (P<0.01). On the other hand, the time required for the group to which Compound A was administered to reach the base was significantly shorter than that for the pathema control group. This indicates that the disorder in the learning function was substantially improved and thus Compound A exhibits an improving effect for cerebral disorder.

2) Influence on Trial Passive Avoidance Training

As a testing apparatus, there was used a training box comprising a bright room whose floor was formed from grid, a dark room capable of applying footshock through the floor made of grid and a port opening equipped with a guillotine door disposed at the boundary of these rooms through which the animal could freely move between these two rooms. First, as an acquired trial, the rat was put in the bright room for 30 seconds while the guillotine door was closed, then the guillotine door was opened and the time required for the rat to enter into the dark room through the guillotine door was determined. After confirming that the rat entered into the dark room, the guillotine door was closed and then a footshock (a current of 0.8 mA; for 2 seconds) was applied to the rat with a shock generator (available from Muromachi Machinery under the trade name of Scrambler SGS-002T) to have the rat learn that it would get an antipathic stimulation in the dark room. After 24 hours, the rat was again put in the bright room, 30 seconds thereafter the guillotine door was opened and the time required for the animal to confirm the entrance and to enter into the dark room (the reaction latency) was determined. The reaction latency was used as an indication of the ability of maintaining the learned memory. In this respect, the measurement was interrupted after 300 seconds and the reaction latency which exceeded 300 seconds was considered to be 300 seconds. The results observed are summarized in the following Table 5.

TABLE 5

| Group | Dose (Oral Route) | Reaction Latency (sec.) |
|---|---|---|
| Pseudo-Operated Group | — | 298.7 ± 1.33** |
| Pathema Control Group | Solvent | 146.7 ± 30.42 |
| Compound A | 10 mg/kg | 271.1 ± 19.21** |
| Compound A | 30 mg/kg | 280.8 ± 19.25** |

The numerical value in Table 5 means average ± standard error.
**: $P < 0.01$ vs. Pathema Control Group (one-way layout variance analysis and Fisher's LSD).
Solvent: 0.5% aqueous methyl cellulose solution.

As seen from Table 5, the average reaction latency (the time required for the rat placed in the bright room to enter into the dark room) for the pathema control group was significantly lower than that for the pseudo-operated group. This clearly indicates that the animals of the pathema control group had a damaged passive avoidance function (P<0.01). On the contrary, the average reaction latency of the group to which Compound A was administered was significantly longer than that for the pathema control group and the passive avoidance failure wa substantially suppressed and thus it could be conclude that Compound A exhibited cerebral disorder improving effect.

3) Influence on the Activity of Choline acetyltransferase (ChAT)

After completion of the learning test, the rat was sacrificed by decapitation and the activity of ChAT which had been believed to be involved in the memory function of animals was determined. The brain tissues were homogenized in 0.05% Triton X-100 containing-phosphate buffer solution (pH 7.4) and the resulting supernatant was used as a sample for determining the ChAT activity. The activity of ChAT was determined according to the method of Fonnum (J. Neurochem., 1975,24, p. 407). The results on the activity of ChAT in the striatum thus determined are listed in the following table 6.

TABLE 6

| Group | Dose (Oral Route) | ChAT (n mol/mg Protein) |
|---|---|---|
| Pseudo-Operated Group | — | 3.70 ± 0.146 |
| Pathema Control Group | Solvent | 3.43 ± 0.097 |
| Compound A | 10 mg/kg | 3.84 ± 0.102* |
| Compound A | 30 mg/kg | 3.94 ± 0.201** |

The numerical value in Table 6 means average ± standard error.
*: $P < 0.05$.
**: $P < 0.01$ vs. Pathema Control Group (one-way layout variance analysis and Fisher's LSD).
Solvent: 0.5% aqueous methyl cellulose solution.

Thus, it was confirmed that Compound A inhibited the lowering of the activity of ChAT in the striatum due to the cerebral ischemia and hence, exhibits an improving effect for the cerebral disorder.

EXAMPLE 4

Compound A was orally administered to rats to determine the acute toxicity thereof. As a result, $LD_{50}$ of Compound A was found to be 293 mg/kg.

We claim:

1. A method for improving cerebral function which comprises administering an effective amount of a compound represented by Formula (I) or salts thereof to a patient suffering from a disease which is accompanied by a lowering of cerebral function:

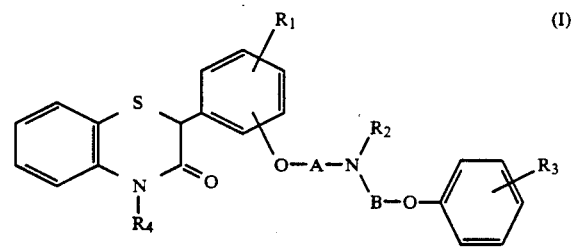

wherein $R_1$ represents one or more functional groups selected from the group consisting of a hydrogen atom, a lower alkyl group, a halogen atom, a nitro group, a hydroxyl group, a lower alkylamino group and a lower alkoxycarbonyloxy group; $R_2$ represents a hydrogen atom, a lower alkyl group or a cycloalkyl group having 3 to 6 carbon atoms; $R_3$ represents one or more functional groups selected from the group consisting of a hydrogen atom, a lower alkyl group, a halogen atom, a nitro group, a hydroxyl group, a lower alkoxy group, a lower alkylenedioxy group, a lower alkanoyl group, a lower alkanoyloxy group, an amino group, a lower alkylamino group, a lower alkanoylamino group and a lower alkoxycarbonyloxy group, or a group:

$R_4$ represents a hydrogen atom or a lower alkyl group; A and B may be the same or different and each represents a lower alkylene group having 1 to 6 carbon atoms; and n is 3 or 4.

2. The method according to claim 1, wherein $R_1$ represents a lower alkoxy group, $R_2$ represents a lower alkyl group; $R_3$ represents a lower alkylenedioxy group; and $R_4$ represents a lower alkyl group or salts thereof.

3. The method according to claim 1, wherein the compound is 3,4-dihydro-2-[5-methoxy-2-[3-[N-methyl-N-[2-[(3,4-methylenedioxy)phenoxy]ethyl]amino]propoxy]phenyl]-4-methyl-3-oxo-2H-1,4-benzothiazine or salts thereof.

4. The method according to claim 3, wherein the compound is (+)-3,4-dihydro-2-[5-methoxy-2-[3-[N-methyl-N-[2-[(3,4-methylenhedioxy) phenoxy]ethyl]amino]propoxy]phenyl]-4-methyl-3-oxo-2H-1,4-benzothiazine or salts thereof.

* * * * *